United States Patent
Jeong et al.

(10) Patent No.: US 8,848,864 B2
(45) Date of Patent: Sep. 30, 2014

(54) TOMOSYNTHESIS SYSTEM

(75) Inventors: Jin Woo Jeong, Daejeon (KR); Yoon Ho Song, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 95 days.

(21) Appl. No.: 13/524,705

(22) Filed: Jun. 15, 2012

(65) Prior Publication Data

US 2013/0003913 A1  Jan. 3, 2013

(30) Foreign Application Priority Data

Jun. 30, 2011  (KR) ........................ 10-2011-0064892

(51) Int. Cl.
- A61B 6/02 (2006.01)
- G01N 23/083 (2006.01)
- H05G 1/60 (2006.01)
- H05G 1/64 (2006.01)
- G01N 23/04 (2006.01)

(52) U.S. Cl.
CPC .................................. *G01N 23/046* (2013.01)
USPC .................................. 378/25; 378/21; 378/22

(58) Field of Classification Search
USPC .................. 378/9, 92, 21, 37, 87, 22, 25, 26, 378/121–124; 977/742
See application file for complete search history.

(56) References Cited

U.S. PATENT DOCUMENTS

| | | | |
|---|---|---|---|
| 4,289,969 A * | 9/1981 | Cooperstein et al. | 378/9 |
| 4,349,740 A * | 9/1982 | Grassmann et al. | 378/25 |
| 6,259,765 B1 * | 7/2001 | Baptist | 378/136 |
| 6,333,968 B1 * | 12/2001 | Whitlock et al. | 378/136 |
| 7,082,182 B2 * | 7/2006 | Zhou et al. | 378/10 |
| 7,085,350 B2 * | 8/2006 | Dunham et al. | 378/119 |
| 7,085,351 B2 * | 8/2006 | Lu et al. | 378/122 |
| 7,085,352 B2 * | 8/2006 | Dunham | 378/122 |
| 7,192,031 B2 * | 3/2007 | Dunham et al. | 378/122 |
| 7,233,644 B1 * | 6/2007 | Bendahan et al. | 378/57 |
| 7,295,651 B2 * | 11/2007 | Delgado et al. | 378/92 |
| 7,627,087 B2 * | 12/2009 | Zou et al. | 378/122 |
| 7,751,528 B2 | 7/2010 | Zhou et al. | |
| 7,809,114 B2 * | 10/2010 | Zou et al. | 378/122 |
| 7,826,594 B2 * | 11/2010 | Zou et al. | 378/92 |
| 7,844,032 B2 * | 11/2010 | Vermilyea et al. | 378/149 |
| 7,873,146 B2 * | 1/2011 | Okunuki et al. | 378/122 |
| 7,940,888 B2 * | 5/2011 | Tsujii | 378/21 |
| 7,991,114 B2 * | 8/2011 | Okunuki et al. | 378/62 |
| 7,991,120 B2 * | 8/2011 | Okunuki et al. | 378/124 |
| 8,155,273 B2 * | 4/2012 | Eaton et al. | 378/136 |
| 8,199,881 B2 * | 6/2012 | Kim et al. | 378/122 |
| 8,208,603 B2 * | 6/2012 | Sato | 378/119 |
| 8,220,993 B2 * | 7/2012 | Takahashi | 378/207 |
| 8,295,441 B2 * | 10/2012 | Beyerlein et al. | 378/134 |
| 8,300,769 B2 * | 10/2012 | Kim et al. | 378/122 |
| 8,306,184 B2 * | 11/2012 | Chang et al. | 378/62 |
| 8,428,221 B2 * | 4/2013 | Boese et al. | 378/122 |
| 8,447,013 B2 * | 5/2013 | Sprenger et al. | 378/122 |
| 8,472,586 B2 * | 6/2013 | Ueda et al. | 378/121 |
| 8,503,614 B2 * | 8/2013 | Legagneux et al. | 378/122 |
| 8,509,380 B2 * | 8/2013 | Pelc et al. | 378/9 |

(Continued)

*Primary Examiner* — Allen C. Ho
(74) *Attorney, Agent, or Firm* — Rabin & Berdo, P.C.

(57) ABSTRACT

Disclosed is a tomosynthesis system in which the maintenance is easily performed. The tomosynthesis system of the present disclosure includes a vacuum chamber, a plurality of X-ray sources configured to be coupled to the vacuum chamber so as to protrude from the vacuum chamber to generate X-rays in a direction of a subject, and an image sensor configured to detect an X-ray projection image that passes through the subject.

9 Claims, 4 Drawing Sheets

(56) References Cited

U.S. PATENT DOCUMENTS

| | | | |
|---|---|---|---|
| 8,588,372 B2 * | 11/2013 | Zou et al. | 378/113 |
| 8,619,946 B2 * | 12/2013 | Hanke et al. | 378/124 |
| 2009/0022264 A1 | 1/2009 | Zhou et al. | |
| 2010/0034450 A1 * | 2/2010 | Mertelmeier | 382/131 |
| 2011/0002442 A1 | 1/2011 | Thran et al. | |
| 2011/0058651 A1 * | 3/2011 | Fuerst et al. | 378/58 |

\* cited by examiner

TOMOSYNTHESIS SYSTEM

CROSS-REFERENCE TO RELATED APPLICATIONS

This application is based on and claims priority from Korean Patent Application No. 10-2011-0064892, filed on Jun. 30, 2011, with the Korean Intellectual Property Office, the disclosure of which is incorporated herein in its entirety by reference.

TECHNICAL FIELD

The present disclosure relates to a tomosynthesis system, and more particularly, to a tomosynthesis system including a plurality of X-ray sources.

BACKGROUND

A computed tomography (CT) system according to a related art irradiates X-rays onto a subject to create X-ray projection images while rotating one X-ray source and synthesizes the images to create a three-dimensional image. In contrast, a tomosynthesis system that synthesizes plural X-ray projection images created by X-rays irradiated onto the subject at different angles from a plurality of X-ray sources has been studied and developed in recent years. The above system allows for rapidly creating tomosynthesis images of separated parts of a soft tissue with a radiation quantity lower than the CT system according to a related art.

However, the tomosynthesis system suggested in the related art is configured such that a plurality of X-ray sources are disposed in one vacuum chamber to be driven. In this case, even if only one of the plurality of X-ray sources malfunctions, the entire system should be disassembled to fix the malfunction, which causes difficulty in maintenance. It is also difficult to adjust the angles of the X-ray sources.

SUMMARY

The present disclosure has been made in an effort to provide a tomosynthesis system where maintenance is easily performed, an X-ray generating angle is easily adjusted, and specifically, a plurality of X-ray sources provided in the system are easily controlled.

An exemplary embodiment of the present disclosure provides a tomosynthesis system, including: a vacuum chamber; a plurality of X-ray sources configured to be coupled to the vacuum chamber so as to protrude from the vacuum chamber to generate X-rays in a direction of a subject; and an image sensor configured to detect an X-ray projection image that passes through the subject.

According to the exemplary embodiment of the present disclosure, the X-ray sources may include: a first coupling module configured to include an electric field emission source that emits electrons and be coupled to the vacuum chamber; a target metal module configured to collide with the electrons to emit X-ray; and a second coupling module configured to be coupled between the first coupling module and the target metal module and serve as a propagation path of the electrons.

The plurality of X-ray sources may be disposed at the outside of the vacuum chamber so as to be apart from each other and sequentially emit the X-rays in the direction of the subject at different angles. The plurality of X-ray sources are coupled to the vacuum chamber so as to be separated from the vacuum chamber and an emission angle of the X-rays can be adjusted.

The tomosynthesis system of the present disclosure may further include an image processor configured to create a three-dimensional image for the subject using the detection result of the image sensor.

According to the exemplary embodiments of the present disclosure, a plurality of X-ray sources provided in a tomosynthesis system are combined at the outside of the vacuum chamber so as to protrude from the vacuum chamber so that when one of the plurality of X-ray sources malfunctions, only the corresponding X-ray source is separately fixed or replaced without disassembling the entire system. Field emission sources provided in the X-ray sources are easily separated. Therefore, it is easy to maintain the entire system.

The X-ray emission angle of the X-ray sources is easily adjusted, so that the direction of the emitted X-rays is maintained at an optimal state.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

In the following detailed description, reference is made to the accompanying drawing, which form a part hereof. The illustrative embodiments described in the detailed description, drawing, and claims are not meant to be limiting. Other embodiments may be utilized, and other changes may be made, without departing from the spirit or scope of the subject matter presented here.

The above-mentioned objects, features and advantages will be described below in detail with reference to the accompanying drawings so that a person with ordinary skill in the art to which the present disclosure pertains may easily perform the technical ideas of the present disclosure. In the following description, well-known arts will not be described in detail when it is judged that they may unnecessarily obscure the present disclosure. Hereinafter, exemplary embodiments of the present disclosure will be described in detail with reference to the accompanying drawings.

Figure 1:
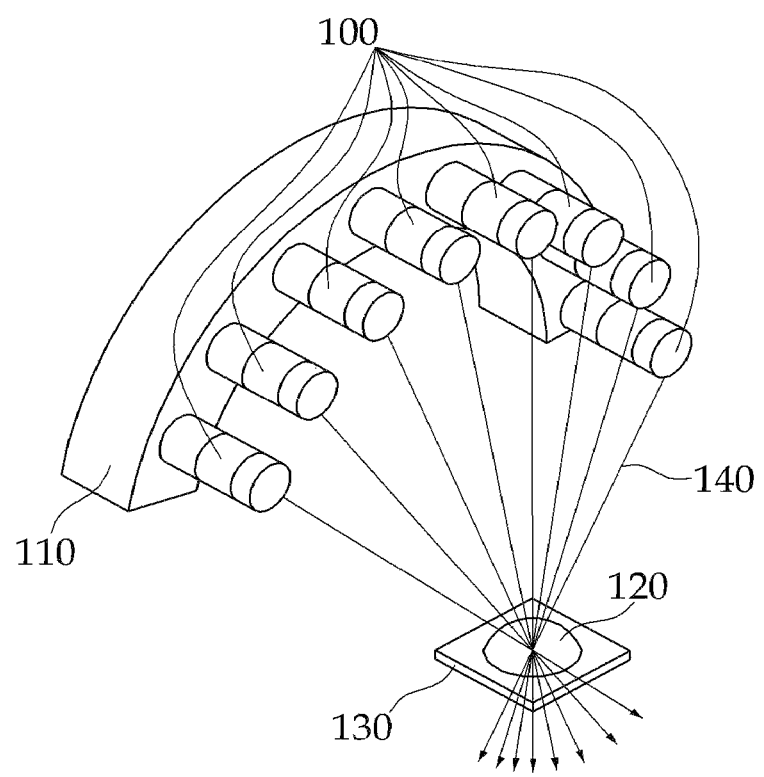
FIG. 1 is a configuration diagram of a tomosynthesis system according to a first embodiment of the present disclosure.
Figure 2:
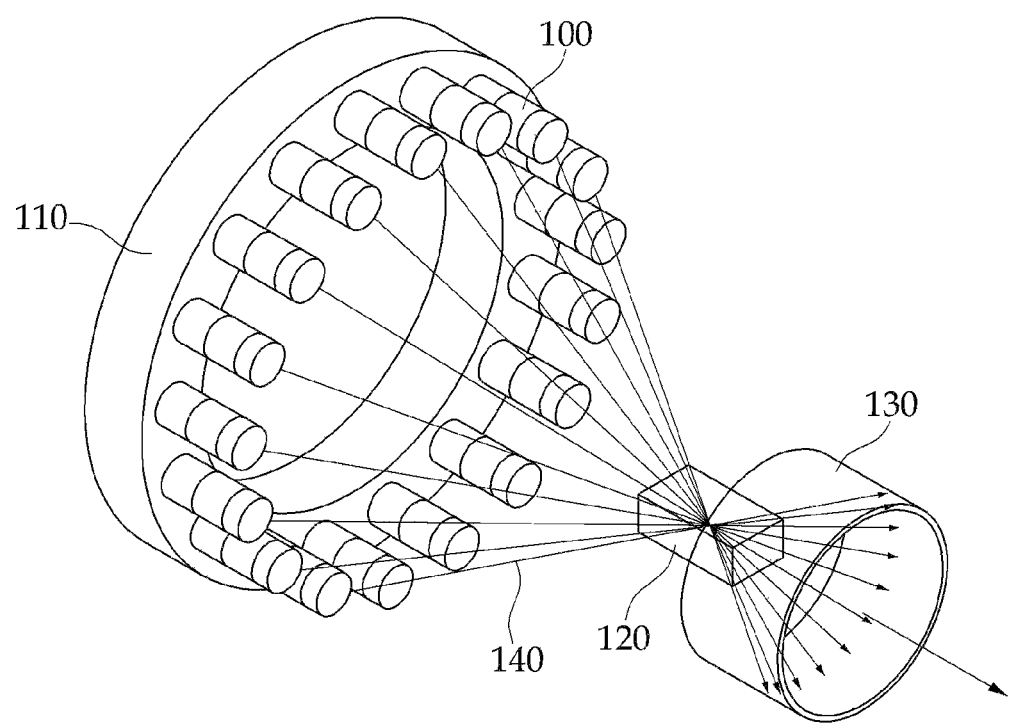
FIG. 2 is a configuration diagram of a tomosynthesis system according to a second embodiment of the present disclosure.
Figure 3:
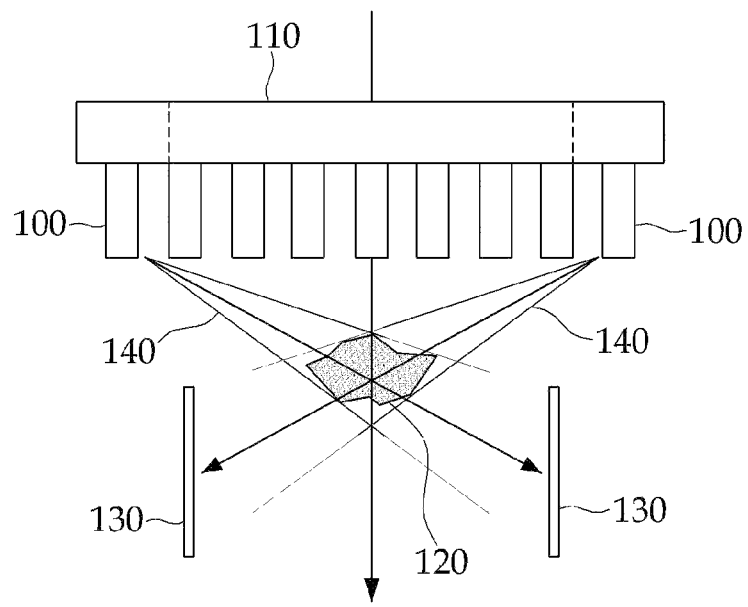
FIG. 3 shows that emitted X-rays 140 pass through a subject 120 to be projected on an image sensor 130.

FIGS. 1 and 2 are configuration diagrams of a tomosynthesis system according to first and second embodiments of the present disclosure and FIG. 3 shows that emitted X-rays 140 pass through a subject 120 to be projected on an image sensor 130.

Referring to FIGS. 1 and 2, a tomosynthesis system according to a present disclosure includes a vacuum chamber 110, a plurality of X-ray sources 100 that are coupled to the vacuum chamber 110 so as to protrude from the vacuum chamber 110 to emit X-rays 140 in a direction of a subject 120, and an image sensor 130 that detects an X-ray projection image that passes through the subject 120.

The plurality of X-ray sources 100 are coupled to the vacuum chamber 110 so as to protrude from an external surface of the vacuum chamber 110 and emit X-rays 140 in a direction where the subject 120 is located. As shown in FIG. 3, when the plurality of X-ray sources 100 sequentially emit X-rays 140 onto the subject 120 at different angles, the emitted X-rays 140 pass through the subject 120 so that images are sequentially projected on the image sensor 130 provided at the rear side. In this case, in the plurality of X-ray sources 100, the emission angle of the X-rays 140 is individually adjusted so as to allow the X-rays 140 emitted from the plurality of X-ray sources 100 to be precisely directed to the subject 120.

The vacuum chamber 110 may be formed to be a simple straight line, or may have various shapes such as a circular arc as shown in FIG. 1 or a ring shape as shown in FIG. 2. If the vacuum chamber 110 is formed to have a ring shape as shown in FIG. 2, the system may be configured such that the plurality of X-ray sources 100 are disposed at the outer surface to make a circle so that the image projected by the X-rays 140 that passes through between the vacuum chambers 110 and is irradiated on the subject 120 is detected by the image sensor 130. This type of system may be widely applied when non-destructive inspection should be performed on a plurality of objects in a short time such as airports or museums.

The tomosynthesis system according to the present disclosure may further include an image processing module (not shown in the drawing) that creates a three-dimensional image for the subject 120 using the detection result of the image sensor 130. The image processing module synthesizes and processes the image that is projected on the image sensor 130 by the X-rays 140 emitted from the plurality of X-ray sources 100 using a computer system to create a three-dimensional image. If necessary, a filter that blocks an X-ray at a specific energy band is inserted to obtain a desired objective image.

Figure 4:
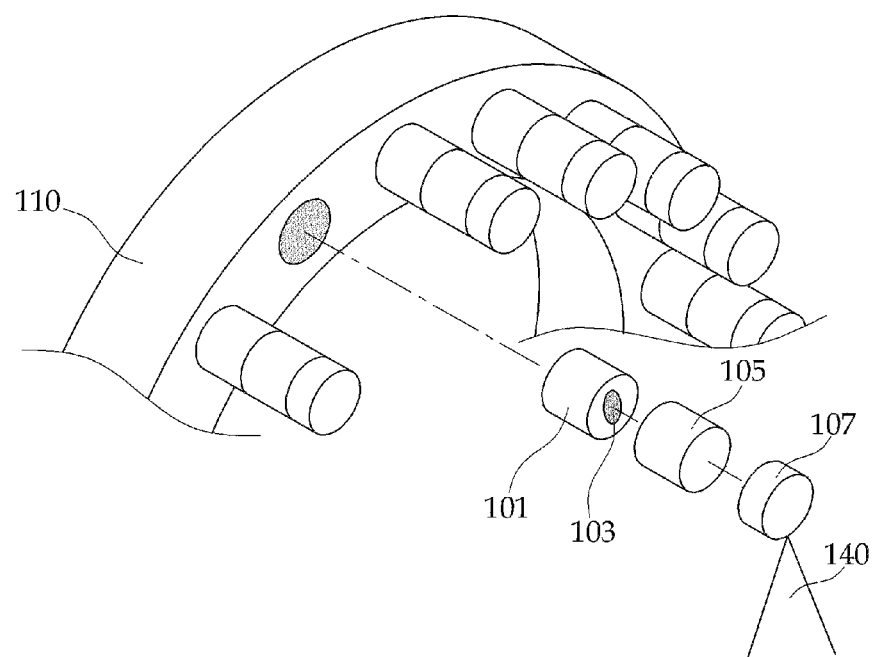
FIG. 4 is a diagram illustrating an X-ray source 100 and a combined portion thereof in detail.

FIG. 4 is a diagram illustrating the X-ray sources 100 of FIGS. 1 and 2 and a combined portion thereof in detail.

Referring to FIG. 4, the plurality of X-ray sources 100 include an electric field emission source 103 that emits an electron, a first coupling module 101 that is coupled to the vacuum chamber 110, a target metal module 107 that collides with emitted electrons to emit the X-rays 140, and a second coupling module 105 that is coupled between the first coupling module 101 and the target metal module 107 and serves as a propagation path of the emitted electrons.

The electric field emission source 103 applies an electric field under a vacuum environment to emit the electrons through a cathode electrode and is configured by an emitter made of nano-scaled materials such as a carbon nano tube (CNT). The target metal module 107 is an anode electrode and emits the X-rays 140 in a predetermined direction when the electron emitted from the electric field emission source 103 collides with the target metal module 107 through an electron transfer path of the second coupling module 105. At this time, by controlling a voltage of the anode electrode, the energy of the emitted X-ray may be varied. Since the detailed configuration and the operation method of the plurality of X-ray sources 100 is widely known in the art, the detailed description thereof will be omitted.

The vacuum chamber 100 may be an open type in which a vacuum pump is connected thereto to operate the vacuum pump whenever the device is driven or a closed type in which the vacuum chamber 100 is sealed so that the vacuum pump is not required.

The plurality of X-ray sources 100 are connected in vacuum state by the vacuum chamber 110 and the first coupling module 101 and the second coupling module 105 are also coupled in vacuum state so as to be separated from each other with respect to the electric field emission source 103. The above coupling modules may have a vacuum coupling structure such as an O-ring or a gasket.

As described above, the plurality of X-ray sources 100 are coupled so as to protrude at the outside of the vacuum chamber 110 so that when one of the plurality of X-ray sources 100 malfunctions, only the corresponding X-ray source is easily replaced without disassembling the entire system. Since the first coupling module 101 and the second coupling module 105 are also separated, only the electric field emission source 103 may be replaced, which allows easy maintenance of the system. Additionally, since the angles of the plurality of X-ray sources 100 are easily adjusted, the direction of the emitted X-rays 140 may be maintained in an optimal status.

Figure 5A:
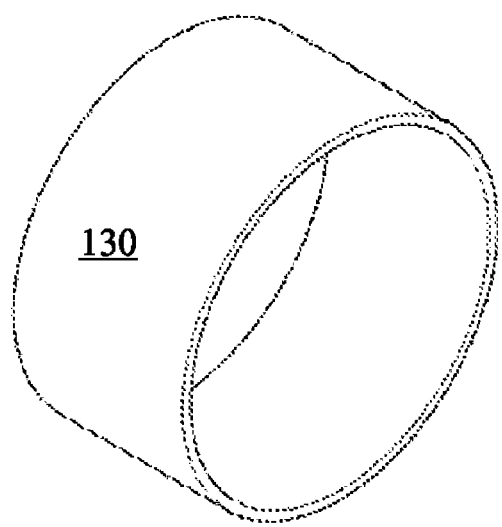
FIGS. 5A and 5B are diagrams of another embodiment of an image sensor 130.
Figure 5B:
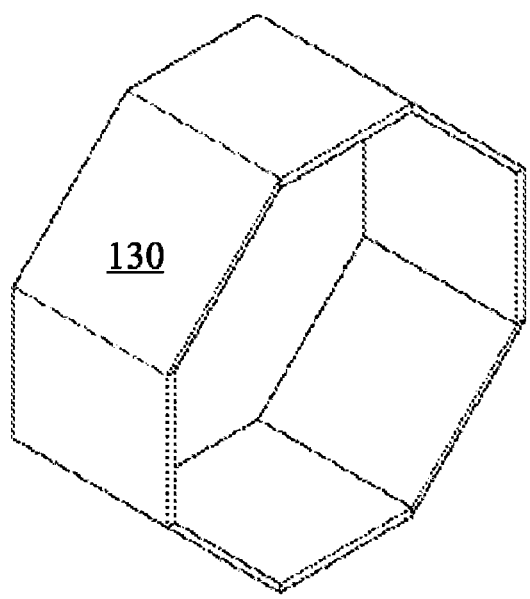

FIGS. 5A and 5B are diagrams of another embodiment of an image sensor 130.

The image sensor 130 of the tomosynthesis system of the present disclosure may be implemented as a cylindrical shape as shown in FIG. 5A or may have a structure in which a plurality of flat sensors are combined as shown in FIG. 5B. It is obvious that the structure and shape of the image sensor 130 may be variously modified in accordance with the purpose and structure of the system.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

What is claimed is:

1. A tomosynthesis system, comprising:
a vacuum chamber;
a plurality of X-ray sources configured to be coupled to the vacuum chamber, the plurality of X-ray sources having an emitting face that is outside of the vacuum chamber to generate X-rays in a direction of a subject; and
an image sensor configured to detect X-rays that pass through the subject;
wherein the plurality of X-ray sources are disposed at the outside of the vacuum chamber so as to be apart from each other and sequentially emit the X-rays in the direction of the subject at different angles.

2. The tomosynthesis system of claim 1, wherein each of the plurality of X-ray sources includes:
a first coupling module configured to include an electric field emission source that emits electrons and be coupled to the vacuum chamber;
a target metal module configured to collide with the electrons to emit the X-rays; and
a second coupling module configured to be coupled between the first coupling module and the target metal module and serve as a propagation path of the electron.

3. The tomosynthesis system of claim 2, wherein the electric field emission source is formed by a carbon nano tube (CNT).

4. The tomosynthesis system of claim 2, wherein the first coupling module and the second coupling module have a vacuum coupling structure.

5. The tomosynthesis system of claim 1, wherein the plurality of X-ray sources are coupled to the vacuum chamber so as to be separable from the vacuum chamber.

6. The tomosynthesis system of claim 1, wherein the plurality of X-ray sources are configured to adjust an emission angle of the X-rays.

7. The tomosynthesis system of claim 1, wherein at least one of the vacuum chamber or the image sensor is formed in a ring shape.

8. The tomosynthesis system of claim 7, wherein when the subject passes through a predetermined position between the vacuum chamber and the image sensor, the X-rays are projected to be detected by the image sensor.

9. The tomosynthesis system of claim 1, further comprising:
   an image processor configured to create a three-dimensional image for the subject using a detection result of the image sensor.

* * * * *